United States Patent
Nakata et al.

(10) Patent No.: US 6,953,504 B2
(45) Date of Patent: Oct. 11, 2005

(54) BLACK PIGMENT POWDER HAVING A LOW VALUE OF MAGNETIZATION, PROCESS FOR PRODUCING THE SAME, AND APPLICATIONS THEREOF

(75) Inventors: Koji Nakata, Yamaguchi-ken (JP); Koji Kurosaki, Yamaguchi-ken (JP); Nobuyuki Hashimoto, Yamaguchi-ken (JP)

(73) Assignee: Titan Kogyo Kabushiki Kaisha, Yamaguchi-ken (JP)

( * ) Notice: Subject to any disclaimer, the term of this patent is extended or adjusted under 35 U.S.C. 154(b) by 108 days.

(21) Appl. No.: 10/733,373

(22) Filed: Dec. 12, 2003

(65) Prior Publication Data

US 2005/0048387 A1 Mar. 3, 2005

(30) Foreign Application Priority Data

Aug. 26, 2003 (JP) ......................... 2003-301574

(51) Int. Cl.$^7$ ................................. C09C 1/36
(52) U.S. Cl. ................. 106/439; 106/456; 106/457; 428/403; 428/404; 430/106.2; 424/63; 424/70.3; 524/413; 524/435
(58) Field of Search ................. 106/439, 456, 106/457, 499; 428/403, 404; 430/106.2; 424/63, 70.7; 524/413, 435

(56) References Cited

FOREIGN PATENT DOCUMENTS

| JP | 3-2276 A | 1/1991 |
| JP | 8-143316 A | 6/1996 |
| JP | 2000-10344 A | 1/2000 |
| JP | 2001-253717 A | 9/2001 |
| JP | 2002-129063 | * 5/2002 ............. C09C/1/36 |

* cited by examiner

Primary Examiner—J. A. Lorengo
Assistant Examiner—S. S. Manlove
(74) Attorney, Agent, or Firm—Birch, Stewart, Kolasch & Birch, LLP

(57) ABSTRACT

A black pigment powder having a low value of magnetization according to the present invention is characterized in that it consists of a composite oxide containing $Fe_2TiO_4$ as a main component, wherein the total amount of Fe (II) and Fe (III) to Ti is from 150 to 300 atomic %, in such an amount that the amount of Fe (II) to the total amount of Fe (II) and Fe (III) is 0.50 or more, and that the L value of a coating according to the Hoover-type muller method is 9.0 or less. It is employed to produce a toner composition, a coating composition, a resin composition, a cosmetic material and the like.

12 Claims, 2 Drawing Sheets in mol%

COMPOSITION IN EACH POINT
($TiO_2$, FeO, $Fe_2O_3$)
A (40.0, 60.0, 0)
B (25.0, 75.0, 0)
C (30.8, 46.2, 23.0)
D (47.1, 35.3, 17.6)

in mol%

COMPOSITION IN EACH POINT
($TiO_2$, FeO, $Fe_2O_3$)
A (40.0, 60.0, 0)
B (25.0, 75.0, 0)
C (30.8, 46.2, 23.0)
D (47.1, 35.3, 17.6)

BLACK PIGMENT POWDER HAVING A LOW VALUE OF MAGNETIZATION, PROCESS FOR PRODUCING THE SAME, AND APPLICATIONS THEREOF

This Non-provisional application claims priority under 35 U.S.C. § 119(a) on Patent Application No(s). 2003-301574 filed in Japan on Aug. 26, 2003, the entire contents of which are hereby incorporated by reference.

BACKGROUND OF THE INVENTION

The present invention relates to a black pigment powder that is-safe and that has no harmful effect on either the environment or the human body; and that is also free of magnetic aggregation. More specifically, the present invention provides a black pigment powder with good dispersibility and high blackness for use as a colorant of a toner, an electrophotography developer, or as a colorant of resins including a coating and a cosmetic material.

Methods of development in electrophotography can be generally divided into a unitary development method, in which development employing a toner itself with a colorant dispersed in a binder resin is employed, and a binary development method, in which development is performed by mixing a toner with a carrier, to thereby cause the toner being carried by the carrier.

In either case, in reproduction, an electrostatic latent image formed on a photosensitive material is developed using one of these toners, and a toner powder having performed image formation on the photosensitive material is transferred onto a transfer material such as a paper or a sheet, and is fixed utilizing heat, pressure or the like to obtain a permanent image. In these toners, a black colorant such as carbon black and magnetite is employed in large amounts to provide an image-forming material. Carbon black is employed in both the binary development method and a non-magnetic unitary development method, while magnetite is employed in the magnetic unitary development method whereby a toner is carried by magnetism.

With the development of computers there has been a corresponding increase in the demand for toners as image-forming materials, and in the use of colorants used in such toners.

However, damage to the environment and to health is a matter of great concern, and consequently, there has been an increasing demand for the safety of raw materials used in toners.

Carbon black, which is employed in large amounts as a black colorant of a toner, contains a small amount of an aromatic hydrocarbon, which contains 3,4-benzpyrene, a substance which has been identified as being carcinogenic. There is therefore an increasing concern in the society about the safety of toners in which carbon black is employed.

In contrast, magnetite is a black pigment comprising safe and harmless iron oxide as a main component, but it suffers from a problem in that since the magnetite particle tends to re-aggregate due to its high value of magnetization, thereby making it difficult to obtain a uniform dispersion. Besides, due to its electrically-conductive properties, it cannot be employed as a colorant of a toner for use in either the binary development method or in the non-magnetic unitary development method requiring insulation properties or high resistance.

As non-magnetic black pigments as a substitute for carbon black, a black pigment particle powder consisting of polycrystalline particles having a mixed composition of $Fe_2TiO_5$ and a $Fe_2O_3$—$FeTiO_3$ solid solution is described in the official gazette of Japanese Patent Public Disclosure (Kokai) No. 2276/1991; and black particle powders having an Mn-containing hematite structure are described in the official gazettes of Japanese Patent Public Disclosure (Kokai) No. 143316/1996 and Japanese Patent Public Disclosure (Kokai) No. 10344/2000.

The black pigment described in Japanese Patent Public Disclosure (Kokai) No. 2276/1991 is a black pigment particle powder consisting of polycrystalline particles having a mixed composition of $Fe_2TiO_5$ (pseudobrookite) and a $Fe_2O_3$ (hematite)-$FeTiO_3$ (ilmenite) solid solution obtained by coating a magnetite particle powder with a titanium compound or calcining a mixed powder of a magnetite particle powder and a titanium compound in a non-oxidative atmosphere; since it comprises harmless iron oxide and titanium oxide as main components, its use does not give rise to problems of safety. However, it suffers from a drawback in that it lacks blackness. Moreover, since the black pigments described in Japanese Patent Public Disclosure (Kokai) No. 143316/1996 and Japanese Patent Public Disclosure (Kokai) No. 10344/2000 contain a large amount of Mn, an environmental pollutant, they cannot be regarded as harmless pigments. In the official gazette of Japanese Patent Public Disclosure (Kokai) No. 253717/2001 there is described a process for obtaining an iron-titanium composite oxide particle powder by a spray thermal decomposition method employing an emulsion containing an aqueous ferrous salt solution, a hydrolytic organic titanium compound and an emulsifier as a spray thermal decomposition solution. However, the process cannot be utilized with existing pigment-producing equipment and requires the use of a spray thermal decomposition device, and is therefore costly.

Thus, to date a black pigment that harms neither the environment nor health, and which has good dispersibility as a substitute for carbon black which has been employed in large amounts as a colorant of a toner for the binary development method and the non-magnetic unitary development method, has not been-produced. There is a great demand for the development of such a black pigment; and such a pigment should also be able to be employed not only as a colorant for a toner but also in resins, including coating materials and cosmetic materials.

SUMMARY OF THE INVENTION AND DESCRIPTION OF THE PREFERRED EMBODIMENTS

In view of the situation outlined above, the present inventors have engaged in assiduous studies upon the development of a black pigment with a low value of magnetization and good dispersibility, which is a composite oxide comprising as main components titanium oxide and iron oxide, neither of which have any harmful effect on either the environment or on health. As typical oxides having blackness comprising titanium oxide and iron oxide as main components can be mentioned $FeTiO_3$ and $Fe_2TiO_4$ (ulvospinel, iron titanium spinel).

The applicant of the present invention has conducted studies on $Fe_2TiO_4$, and found that a black pigment powder having a low value of magnetization, titanium oxide coated with $Fe_2TiO_4$, could be obtained by employing titanium oxide as a substrate, forming $Fe_2TiO_5$ upon the surface thereof and reducing it, this invention being filed under Japanese Patent Application No. 332589/2000. This black pigment powder having a low value of magnetization is useful from the viewpoint of safety, dispersibility and blackness under existing conditions; however, to be employed as a substitute for carbon black and magnetite as toner colorants in future, higher safety, dispersability and blackness are required. Hence, the present inventors have engaged in further assiduous studies and found that a black pigment powder having a low value of magnetization and higher blackness can be obtained by a process comprising the steps of: mixing hydrous or anhydrous titanium oxide with any one or more of iron hydroxide, iron oxide and hydrous iron oxide-in such amount that the total amount of Fe (II) and Fe (III) is of from 150 to 300 atomic % based on Ti; calcining the mixture in an oxidizing atmosphere at a temperature of from 700 to 1100° C. to form a $Fe_2TiO_5$ phase; and further reducing the resulting product to form a $Fe_2TiO_4$ phase. This has led to the completion of the present invention.

Figure 1:
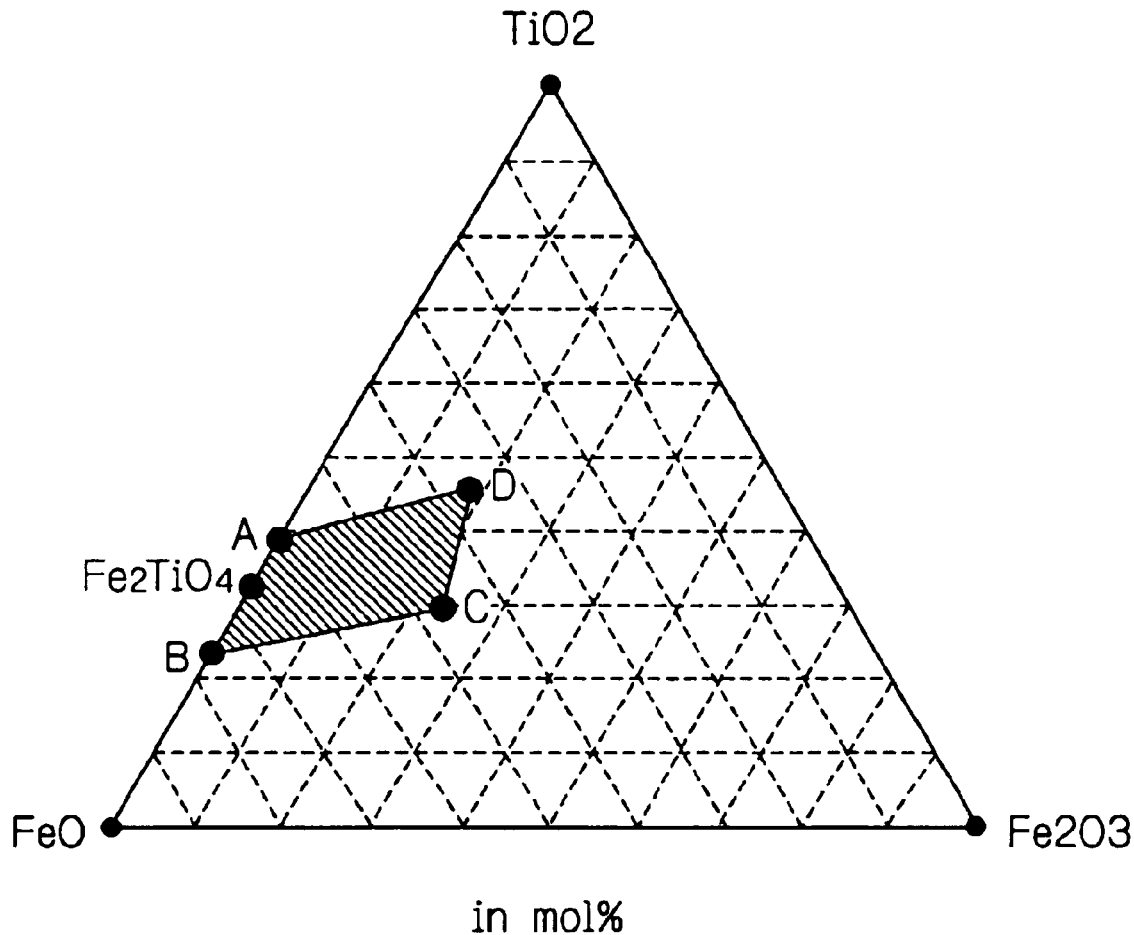
FIG. 1 is a ternary diagram of $TiO_2$, FeO and $Fe_2O_3$, and the range combining points of A to D is the mol composition range of black pigment powder having a low value of magnetization according to the present invention.

That is, the present invention relates to a black pigment powder having a low value of magnetization, which consists of a composite oxide containing $Fe_2TiO_4$ as a main component, wherein the total amount of Fe (II) and Fe (III) is of from 150 to 300 atomic % based on Ti, a ratio of the amount of Fe (II) to the total amount of Fe (II) and Fe (III) is 0.50 or more, and the L value of a coating obtainable from the black pigment powder according to the Hoover-type muller method is 9.0 or less. In the ternary diagram of $TiO_2$, FeO and $Fe_2O_3$ shown in FIG. 1, the composition of a black pigment powder having a low value of magnetization according to the present invention is within the range combining Point A (40.0, 60.0, 0), Point B (25.0, 75.0, 0), Point C (30.8, 46.2, 23.0) and Point D (47.1, 35.3, 17.6).

In addition, the black pigment powder having a low value of magnetization of the present invention has a value of magnetization of from 0.1 to 20.0 $Am^2/kg$ (=emu/g), and is thus an excellent substitute for carbon black.

The black pigment powder having a low value of magnetization of the present invention can be employed as a toner colorant as it is, or preferably is modified such that the surface of the black pigment powder is coated with one or more hydrous or anhydrous inorganic oxides selected from a group consisting of silicon, aluminum, titanium, zirconium and tin. Alternatively, it is preferably subjected to a hydrophobic treatment with a silicone oil and/or a coupling agent to enhance heat resistance and compatibility with a resin and to improve static properties in a toner and environmental stability, on demand. Moreover, these various surface modification treatments may optionally be combined.

The black pigment powder having a low value of magnetization of the present invention can be obtained typically in the following manner. That is, the production process of the present invention relates to a process for producing a black pigment powder having the above characteristics, the process comprising the steps of: mixing hydrous or anhydrous titanium oxide with any one or more of iron hydroxide, iron oxide and hydrous iron oxide in such an amount that the total amount of Fe(II) and Fe(III) is of from 150 to 300 atomic % based on Ti; calcining the mixture in an oxidizing atmosphere at a temperature of from 700 to 1100° C. to form a $Fe_2TiO_5$ phase; and further, reducing the resulting product to form a $Fe_2TiO_4$ phase.

In the process of the present invention, it is important to mix titanium oxide and an iron compound uniformly so as to obtain the desired black pigment powder, and for this purpose, it is necessary to employ materials with high reactivity as raw materials of titanium oxide and an iron compound. Mixing referred to herein includes coating the titanium oxide with the iron compound.

Titanium oxide which may be employed in the present invention preferably has a specific surface area of 20 $m^2/g$ or more. Hydrous titanium hydroxide is particularly preferred from the viewpoint of its higher reactivity due to a specific surface area as high as 200 $m^2/g$. In the case of employing hydrous titanium oxide obtainable by a sulfuric acid method as a raw material, the sulfur content contained in the hydrous titanium oxide has an effect of making it difficult to form a $Fe_2TiO_5$ phase during calcination. Thus, the sulfur should be removed by washing.

In the present invention, any one or more of ferrous hydroxide, ferric hydroxide, hydrous iron oxide and iron oxide may be employed as iron compounds. Moreover, Water-soluble iron salt which may be employed as a raw material includes ferrous chloride, ferric chloride, ferrous sulfate, ferric sulfate, ferrous nitrate and ferric nitrate.

As processes for mixing titanium oxide with an iron compound usable in the present invention there can be mentioned a process for producing ferrous hydroxide or ferric hydroxide by adding ferrous salt or ferric salt to a hydrous or anhydrous titanium oxide slurry and then neutralizing the mixture, and a process for producing hydrous iron oxide or iron oxide by oxidizing the ferrous hydroxide produced by the above method. In the latter case, the particle diameter of the resulting hydrous iron oxide or iron oxide is 0.5 $\mu$m or less, preferably 0.2 $\mu$m or less.

The mixing ratio of iron to titanium, the total amount of Fe (II) and Fe (III) to Ti is of from 150 to 300 atomic %. If the ratio is less than 150 atomic %, the desired blackness cannot be achieved. If the ratio exceeds 300 atomic %, the value of magnetization becomes greater than 20 $Am^2/kg$, and this undesirably results in particle aggregation and a reduction in dispersibility.

The mixture thus obtained of hydrous or anhydrous titanium oxide and any one or more of iron hydroxide, iron oxide and hydrous iron oxide is calcined in an oxidizing atmosphere to form a $Fe_2TiO_5$ phase; the calcination temperature is from 700 to 1,100° C., preferably from 800 to 1,000° C. If the temperature is below 700° C., a $Fe_2TiO_5$ phase is scarcely formed and the blackness decreases undesirably. If the temperature is above 1,100° C., dispersibility becomes poor, and the resulting product is not suitable as a toner colorant.

Then, the $Fe_2TiO_5$ phase obtained by the above calcination process is reduced. As reducing agents which may be employed in the present invention there can be mentioned reducing gases such as hydrogen gas, a mixed gas of hydrogen and carbon dioxide, carbon monoxide gas, ammonium gas and amine gas, and a solid reducing agent containing carbon. If the solid reducing agent containing carbon is used, it is preferable that no carbon black should remain. In the present invention, it is particularly preferred to perform reduction employing a mixed gas of hydrogen and carbon dioxide since $Fe_2TiO_4$ can be stably obtained during reduction. Though reduction can be performed at a temperature of from 250 to 700° C., it is necessary to perform it at an optimum temperature depending on a reducing agent employed. In the case of performing reduction employing a mixed gas of hydrogen and carbon dioxide, the optimum temperature ranges is from 400 to 550° C. In the case of a temperature below 400° C., reduction fails to occur at an appropriate level to produce a sufficient amount of $Fe_2TiO_4$, and this results in an undesirable decrease in blackness. Moreover, if the temperature is over 550° C., sintering of particles occurs during reduction and this results in poor dispersibility.

In the production process of the present invention, a well-known sinter-inhibiting agent such as aluminum, silicon, phosphorus and zirconium salts can be used, if necessary. This process can provide a black pigment powder having a low value of magnetization and excellent dispersibility. An amount of the sinter-inhibiting agent to be added is from 0.05 to 10 weight %, preferably from 0.05 to 5 weight % based on a black pigment powder having a low value of magnetization to be obtained. If the amount of the sinter-inhibiting agent is less than 0.05 weight %, the sinter inhibition effect is poor, and if it exceeds 10 weight %, it is difficult to proceed with the reduction process.

Moreover, in the production process of the present invention, it is preferable to coat the surface of the black pigment powder with any one or more of hydrous or anhydrous inorganic oxides of silicon, aluminum, titanium, zirconium and tin, or with any one or more of a silicone oil, a silane coupling agent and a titanium coupling agent, which are hydrophobic agents; these various surface modification treatments may optionally be combined.

In the case of performing a coating treatment with a hydrous or anhydrous inorganic oxide of silicon, aluminum, titanium, zirconium and tin, it may be performed by a known method. That is, this treatment may be performed by slurrying the obtained black pigment powder having a low value of magnetization with water; water-grinding the slurry by employing a pebble mill, a sand grinder, an attritor or the like; adding any one or more of water-soluble salts of silicon, aluminum, titanium and zirconium; neutralizing the reaction product by use of an alkali or an acid to precipitate a hydrous or anhydrous oxide. Moreover, a hydrophobic treatment by a hydrophobic agent may be performed by a known wet process or dry process. Hydrophobization agents which may be employed include silicon oils such as methyl phenyl polysiloxane, dimethylsiloxane, H-modified polysiloxane and fluorine-modified polysiloxane, and coupling agents such as a silane coupling agent and a titanium coupling agent; they may be combined.

The black pigment powder having a low value of magnetization of the present invention has advantageous effects as a black pigment in a coating material, a resin composition and a cosmetic material.

For use in the coating, it can be employed not only as a general coating colorant, but also as a colorant for a heat-resistant coating.

Moreover, for use in a resin composition, it can be employed not only as a colorant for general-purpose resins such as a vinyl chloride resin, a polyethylene resin and a polypropylene resin, but also as a colorant for thermosetting resins such as an unsaturated polyester resin, an epoxy resin and a polyurethane resin.

Moreover, for use for a cosmetic material, it can be employed as a black pigment for a foundation, eye shadow and an eyebrow pencil.

EXAMPLES

Hereunder, the present invention will be described in accordance with examples and comparative examples, which never limit the present invention.

The L value of a coating containing the black pigment powder of the invention can be determined by use of Hoover-type muller method as follows:

The black pigment powders obtained in the following examples and comparative examples was used to form a coating, wherein 0.5 g of the ground product is kneaded with 3 mL of a styrenated alkyd resin and applied to art paper by a six-mil doctor blade, and baked at 110° C. for 10 minutes to be fixed on the paper. The blackness (L value) of the coating was measured by a color tester SC-2-CH manufactured by Suga Shikenki K. K.

The specific surface area of the obtained powder was measured by Gemini (phonetic) 2375 manufactured by Micromeritics (phonetic).

The value of magnetization of the obtained powder was measured at a magnetic field of 397.9 kA/m (5 kOe) by VSM manufactured by Toei Kogyo.

For a gloss, the gloss of 60°—60° of a coating, blackness of which was measured, was measured by a gloss meter manufactured by Murakami Shikisai Kenkyusho.

Example 1

A hydrous titanium oxide slurry with a specific surface area of 260 m²/g obtained by the sulfuric acid method was adjusted to 150 g/l as titanium oxide, and the pH thereof was adjusted to 9 employing 400 g/l of caustic soda. After stirring for 2 hours, the pH thereof was adjusted to 6 with 200 g/l of hydrochloric acid, and filtration and washing were conducted. The washed hydrous titanium oxide was repulped and adjusted to 100 g/l as titanium oxide, then a ferric chloride solution was added to the slurry in amount of 100 g/l as $Fe_2O_3$ so that the ratio of Fe to Ti should be 170 atomic %, 200 g/l of a caustic soda solution was dropped thereinto, and the pH of the slurry was adjusted to 7 to prepare a mixed slurry of hydrous titanium oxide and iron hydroxide.

The above mixed slurry was filtrated, washed, and dried at 110° C. The dried product was put into a porcelain crucible, and calcined at 950° C. in an electric oven for one hour to form a $Fe_2TiO_5$ phase. After cooling, reduction was performed with a mixed gas of hydrogen and carbon dioxide at 520° C. for 8 hours to reduce the $Fe_2TiO_5$ phase into a $Fe_2TiO_4$ phase, which was ground to obtain a black pigment powder.

Figure 2:
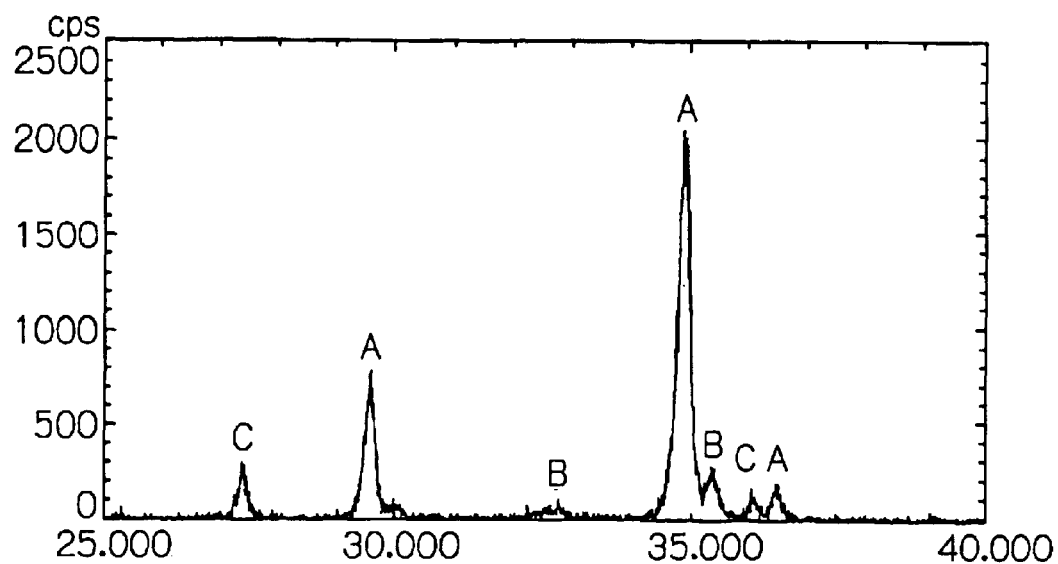
FIG. 2 is an X-ray diffraction diagram of the black pigment powder having a low value of magnetization obtained in Example 1 of the present invention.

FIG. 2 is the X-ray diffraction diagram of the obtained black pigment powder. Peak A in the diagram shows $Fe_2TiO_4$, Peak B shows a $Fe_2O_3FeTiO_3$ solid solution, and Peak C shows rutile-type titanium oxide. That is, it has been found from the X-ray diffraction diagram that the above product is a mixed phase crystal consisting of a composite oxide comprising $Fe_2TiO_4$ as a main component.

Example 2

A hydrous titanium oxide slurry with a specific surface area of 260 m²/g obtained by the sulfuric acid method was adjusted to 150 g/l as titanium oxide, and the pH thereof was adjusted to 9 employing 400 g/l of caustic soda. After stirring for 2 hours, the pH thereof was adjusted to 6 with 200 g/l of hydrochloric acid, and filtration and washing were conducted. The washed hydrous titanium oxide was repulped and adjusted to 100 g/l as titanium oxide, then a ferric chloride solution was added to the slurry in amount of 100 g/l as $Fe_2O_3$ so that the ratio of Fe to Ti should be 230 atomic %, 200g/l of a caustic soda solution was dropped thereinto, and the temperature of the slurry was adjusted to 70° C. and the pH thereof was adjusted to 10 and then air oxidation was performed, and a mixed slurry of magnetite and hydrous titanium oxide was prepared.

The above mixture was filtrated, washed, and dried at 110° C. The dried product was put into a porcelain crucible, and calcined at 850° C. in an electric oven for one hour to form a $Fe_2TiO_5$ phase. After cooling, it was reduced with a mixed gas of hydrogen and carbon dioxide at 520° C. for 8 hours and ground to obtain a black pigment powder.

Figure 3:
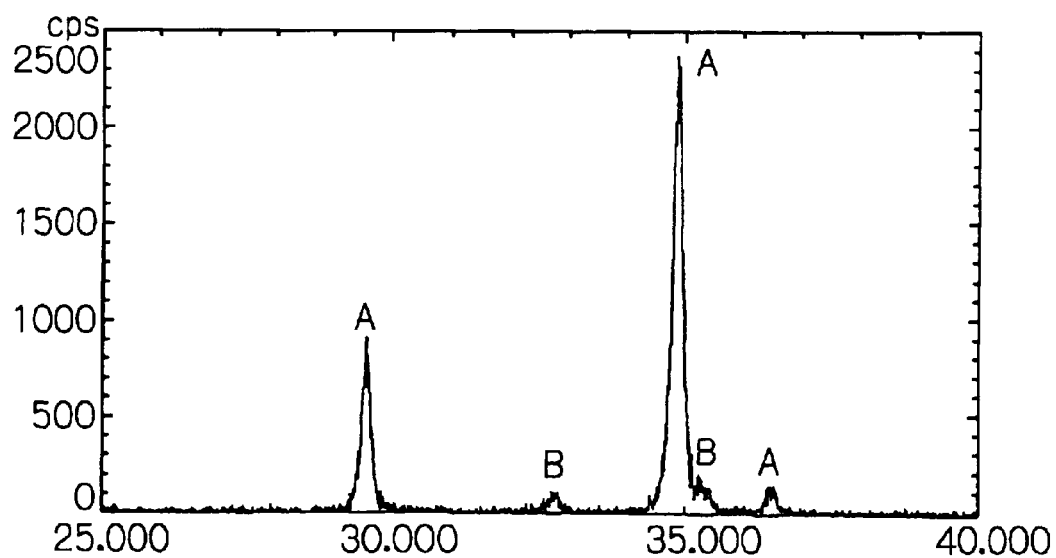
FIG. 3 is an X-ray diffraction diagram of the black pigment powder having a low value of magnetization obtained in Example 2 of the present invention.

FIG. 3 is the X-ray diffraction diagram of the obtained black pigment powder. Peak A in the diagram shows $Fe_2TiO_4$, and Peak B shows a $Fe_2O_3$—$FeTiO_3$ solid solution. That is, it has been found from the X-ray diffraction diagram that the above product is a mixed phase crystal consisting of a composite oxide comprising $Fe_2TiO_4$ as a main component.

Example 3, Comparative Examples 1 & 2

The ratio of Fe to Ti ((Fe (II)+Fe (III))/Ti), the calcining temperature, the reduction temperature and the reduction time in Example 1 were changed as shown in Table 1 to synthesize black pigment powders.

TABLE 1

Production Conditions and Characteristics of Black Pigments having a low value of magnetization

|  | (Fe(II) + Fe(III))/Ti atomic % | Sinter. temp. ° C. | Reduc. Temp. ° C. | Reduc. time h | Fe(II)/(Fe(II) + Fe(III)) % |
|---|---|---|---|---|---|
| Ex. 1 | 170 | 950 | 520 | 8 | 0.798 |
| Ex. 2 | 230 | 850 | 520 | 8 | 0.724 |
| Ex. 3 | 284 | 950 | 520 | 8 | 0.711 |
| Comp. Ex. 1 | 100 | 900 | 500 | 5 | 0.560 |
| Comp. Ex. 2 | 200 | 900 | 500 | 5 | 0.469 |

|  | Specific surface area $m^2/g$ | Value of Magnetization $Am^2/kg$ | L value | Gloss % |
|---|---|---|---|---|
| Ex. 1 | 4.4 | 4.6 | 8.3 | 73.4 |
| Ex. 2 | 8.8 | 8.9 | 8.5 | 74.2 |
| Ex. 3 | 4.9 | 15.8 | 7.3 | 63.1 |
| Comp. Ex. 1 | 6.7 | 6.5 | 9.8 | 72.5 |
| Comp. Ex. 2 | 6.3 | 1.3 | 15.7 | 78.6 |

Example 4

After the black pigment powder obtained in Example 1 was repulped in pure water and water-ground by a sand grinder, it was heated to 70° C., and 2.5 weight % of an aluminum sulfate solution was added as $Al_2O_3$ to the black pigment powder while stirring well. Subsequently, a sodium hydroxide solution was added to the reaction product to adjust the pH to 7.5, and coating with aluminum hydroxide was performed. After aging for one hour, filtration, washing, drying and grinding were performed to obtain an $Al_2O_3$-coated black pigment powder.

The gloss of 60°—60° of a coating containing the obtained black pigment powder was measured; it was 77.2%, showing improved dispersibility relative to that of Example 1.

Example 5

In Example 4, after coating with aluminum hydroxide, 5 weight % of hexyltrimethoxysilane was added to the black pigment powder; hydrolysis was performed in water, a treatment with a silane coupling agent was performed, and filtration, washing, drying and grinding were performed to obtain a silane-coupling-agent-coated black pigment powder.

The gloss of 60°—60° of a coating containing the obtained black pigment powder was measured; it was 80.1%, showing further improved dispersibility relative to that of Example 4.

As is apparent from the results of Table 1, since the black pigment powder having a low value of magnetization of the present invention can be used to form a coating having a L value of 9.0 or less according to the Hoover-type muller method, it has blackness equivalent to that of magnetite; besides, the value of magnetization is 20 $Am^2/kg$ or less and the gloss is good, and hence, it scarcely shows magnetic aggregation and exhibits good dispersibility.

Effects of the Invention

The black composite oxide of the present invention is a safe and harmless black pigment having a low value of magnetization, and it scarcely shows magnetic aggregation and exhibits good dispersibility; hence, it is suitable as a colorant of an electrostatic development toner, a coating, a resin and a cosmetic material and the like.

What is claimed is:

1. A black pigment powder having a low value of magnetization, which comprises a composite oxide containing $Fe_2TiO_4$ as a main component, wherein the total amount of Fe (II) and Fe (III) is from 150 to 300 atomic % based on Ti, the ratio of the amount of Fe (II) to the total amount of Fe (II) and Fe (III) is 0.50 or more, and the L value of a coating containing the black pigment powder is 9.0 or less according to the Hoover-type muller method.

2. A black pigment powder having a low value of magnetization according to claim 1, wherein the value of magnetization is from 0.1 to 20.0 $Am^2/kg$.

3. A black pigment powder having a low value of magnetization according to claim 1 or 2, wherein the powder is coated with one or more hydrous or anhydrous inorganic oxides selected from the group consisting of silicon, aluminum, titanium, zirconium and tin.

4. A black pigment powder having a low value of magnetization according to claim 1 or 2, wherein the powder is subjected to a hydrophobic treatment with a silicone oil and/or a coupling agent.

5. A black pigment powder having a low value of magnetization according to claim 3, wherein the powder is subjected to a hydrophobic treatment with a silicone oil and/or a coupling agent.

6. A process for producing a black pigment powder having a low value of magnetization according to claim 1, which comprises mixing hydrous or anhydrous titanium oxide with one or more of iron hydroxide, iron oxide and hydrous iron oxide in such an amount that the total amount of Fe (II) and Fe (III) to Ti is from 150 to 300 atomic %, calcining the mixture in an oxidizing atmosphere at a temperature of from 700 to 1100° C. to form a $Fe_2TiO_5$ phase, and reducing the resulting product to form a $Fe_2TiO_4$ phase.

7. A process for producing a black pigment powder having a low value of magnetization according to claim 6, wherein hydrous titanium oxide having a specific surface area of 200 $m^2/g$ or more is employed as a substrate.

8. A process for producing a black pigment powder having a low value of magnetization according to claim 6 or 7, wherein a mixed gas of hydrogen and carbon dioxide is employed as a reducing agent, and reduction is performed at a temperature of form 400 to 550° C.

9. A toner composition comprising a black pigment powder having a low value of magnetization according to claim 1 or 2.

10. A coating comprising a black pigment powder having a low value of magnetization according to claim 1 or 2.

11. A resin composition comprising a black pigment powder having a low value of magnetization according to claim 1 or 2.

12. A cosmetic material comprising a black pigment powder having a low value of magnetization according to claim 1 or 2.

* * * * *